(12) United States Patent
Zhao et al.

(10) Patent No.: US 10,130,080 B2
(45) Date of Patent: Nov. 20, 2018

(54) OBESITY ANIMAL MODEL AND METHODS FOR MAKING AND USING THEREOF

(71) Applicants: SHANGHAI JIAO TONG UNIVERSITY, Shanghai (CN); PERFECT (CHINA) CO., LTD, Zhongshan (CN)

(72) Inventors: Liping Zhao, Shanghai (CN); Na Fei, Shanghai (CN)

(73) Assignees: SHANGHAI JIAO TONG UNIVERSITY, Shanghai (CN); PERFECT (CHINA) CO., LTD., Zhongshan (CN)

( * ) Notice: Subject to any disclaimer, the term of this patent is extended or adjusted under 35 U.S.C. 154(b) by 380 days.

(21) Appl. No.: 14/420,410

(22) PCT Filed: Aug. 1, 2013

(86) PCT No.: PCT/CN2013/080589
§ 371 (c)(1),
(2) Date: Feb. 9, 2015

(87) PCT Pub. No.: WO2014/023178
PCT Pub. Date: Feb. 13, 2014

(65) Prior Publication Data
US 2015/0208620 A1    Jul. 30, 2015

(30) Foreign Application Priority Data

Aug. 8, 2012  (CN) .......................... 2012 1 0280927

(51) Int. Cl.
*A01K 67/00* (2006.01)
*A01K 67/027* (2006.01)
*A61K 49/00* (2006.01)

(52) U.S. Cl.
CPC ...... *A01K 67/0271* (2013.01); *A61K 49/0008* (2013.01); *A01K 2207/12* (2013.01); *A01K 2207/25* (2013.01); *A01K 2227/105* (2013.01); *A01K 2267/0337* (2013.01); *A01K 2267/0362* (2013.01); *A01K 2267/0368* (2013.01)

(58) Field of Classification Search
CPC .................... A01K 67/0271; A61K 49/0008
See application file for complete search history.

(56) References Cited

U.S. PATENT DOCUMENTS

| 2,880,309 A | 3/1959 | Gallagher |
| 8,748,123 B2 * | 6/2014 | Carvalho Fernandes De Miranda Reis ......... C12P 19/04 435/41 |
| 2006/0046246 A1 * | 3/2006 | Zeng ..................... G06F 19/22 435/5 |
| 2015/0208620 A1 | 7/2015 | Zhao et al. |

FOREIGN PATENT DOCUMENTS

| EP | 1790220 A1 | 5/2007 |
| WO | WO2010146568 A1 | 12/2010 |
| WO | WO2011013106 A1 | 2/2011 |
| WO | WO2012024638 A2 | 2/2012 |

OTHER PUBLICATIONS

Drel et al. Diabetes 55:3335-3343, 2006.*
Model definition printout from Google. www.google.com. p. 1-3, printed Jan. 4, 2017.*
Fredrik Backhed et al.,The gut microbiota as an environmental factor that regulates fat storage, p. 15718-15723, PNAS, vol. 101, No. 44, Nov. 2, 2004.
Patrice D. Cani et al., Metabolic Endotoxemia Initiates Obesity and Insulin Resistance, p. 1761-1772, Diabetes, vol. 56, Jul. 2007.
Patrice D. Cani et al., Changes in Gut Microbiota Control Metabolic Endotoxemia-Induced Inflammation in High-Fat Diet-Induced Obesity and Diabetes in Mice, p. 1470-1481, Diabetes, vol. 57, Jun. 2008.
Yunhui Liu, et al., Research progress on gut microbiota and obesity and the relevant metabolic disorder inflammation, p. 137-140, Advancing of physiological science, vol. 43, No. 2, 2012.
Ling Xie et al., Relationship between obesity, relevant metabolic disorders and intestinal flora, p. 6-14, Int J Dig Dis, vol. 32, No. 1, Feb. 2012.
Patrice D Cani et al., Interplay between obesity and associated metabolic disorders:new insights into the gut microbiota, Current Opinion in Pharmacology 9:737-743, 2009.
Shen Ding-shu, Gut microbial ecosystem and obesity, Chinese Journal of Microecology, p. 91-92, vol. 24, No. 1, 2012, abstract only.
Zhao Li-ping et al., Functional dynamics of gut microbiota in obesity and metabolic diseases, Chinese Bulletin of Life Sciences, vol. 22, No. 12, Dec. 2010, abstract only.
Office Action of Corresponding Canadian patent application 2,880,309, dated Feb. 12, 2016.
Supplementary European search report of EP 13827097.0, dated, Feb. 19, 2016.
Terenius O1, De Oliveira CD, Pinheiro WD, Tadei Mari Notti O.:"16S rRNA gene sequences from bacteria adult *Anopheles darlingi* (Diptera: culicidae) mosquitoes.",J Med Entomol, 45(1):172-175 (2008).
Chavshin AR, Oshaghi MA, Vatandoost H, Pourmand MR,Raeisi A, Enayati AA, Mardani N, Ghoorchian S.: "Identification of bacterial microflora in the midgut of the larvae and adult of wild caught*Anopheles stephensi*:a step toward finding suitable paratransgenesis candidates." Acta Trop., 121(2):129-34, Feb. 2012.

(Continued)

*Primary Examiner* — Marcia S Noble
(74) *Attorney, Agent, or Firm* — Zhihua Han; Le Tian (57) ABSTRACT

The application provides, among others, methods for constructing animal obesity models, methods for screening microorganism or composition of microorganisms that may cause obesity, methods for screening therapeutic targets for treating metabolic disorders, and methods for screening or evaluating microorganisms, compounds, food, recipes, formulations, drugs, nutritional supplements, healthcare products, beverages and other items for preventing and treating metabolic diseases.

5 Claims, 3 Drawing Sheets
Specification includes a Sequence Listing.

(56) References Cited

OTHER PUBLICATIONS

Patrice D. Cant et al: "Involvement of gut microbiota in the development of low-grade inflammation and type 2 diabetes associated with obesity", Gut Microbes; Aug. 2012.

Shengli Ding et al: "High Fat Diet: Bacteria Interactions Promote Intestinal Inflammation Which Precedes and Correlates with Obesity and Insulin Resistance in Mouse", PLoS One; vol. 5, issue 8, Aug. 2010.

S. Rabot et al: "Germ-free C57BL/6J mice are resistant to high-fat-diet-induced insulin resistance and have altered cholesterol metabolism", The FASEB Journal ;24(12):4948-59, Dec. 2010.

Fredrik Backhed, et al., Mechanisms underlying the resistance to diet-induced obesity in germ-free mice; PNAS, vol. 104, No. 3, 979-984, Jan. 16, 2007.

Yolanda Sanz, et al., Gut microbiota in obesity and metabolic disorders, Proceedings of the Nutrition Society, 69, 434-441, 2010.

Ana Paula Boroni Moreira, et al., Influence of a high-fat diet on gut microbiota, intestinal permeability and metabolic endotoxaemia, British Journal of Nutrition, 108, 801-809, 2012.

A.P. Boroni Moreira, et al., The influence of endotoxemia on the molecular mechanisms of insulin resistance, Nutrition Hospitalaria, 27(2): 382-390, 2012.

Rosa Krajmanlnik-Brown, et al, Effects of Gut Microbes on Nutrient Absorption and Energy Regulation, Nutr Clin Pract. 27(2):201-214, Apr. 2012.

Neyrinck AM, et al., Dietary modulation of clostridial cluster XIVa gut bacteria (*Roseburia* spp.) by chitin-glucan fiber Improves host metabolic alterations induced by high-fat diet in mice, J Nutr Biochem.;23(1):51-9, Jan. 2012.

Zhang C, et al., Interactions between gut microbiota, host genetics and diet relevant to development of metabolic syndromes in mice, ISME J.;4(2):232-41. Feb. 2010.

Zhang C, et al., Structural resilience of the gut microbiota in adult mice under high-fat dietary perturbations, ISME J.;6(10)1848-57, Oct. 2012.

Search Report and Written Opinion of 11201500785T issued by IPOS dated Jan. 22, 2016.

Second Written Opinion of 11201500785T issued by IPO dated Oct. 28, 2016.

DiBaise JK, et al., Gut microbiota and its possible relationship with obesity, Mayo Clin Proc.;83(4):460-9, Apr. 2008.

Office Action of Corresponding Australian patent application 2013302036, dated Jul. 8, 2016.

First Office Action of Corresponding Russian patent application 2015108075, dated 2016.

Second Office Action of Corresponding Russian patent application 2015108075, dated 2016.

Na Fei, et al., An opportunistic pathogen isolated from the gut of an obese human causes obesity in germfree mice, ISME journal 7(4), 2012.

\* cited by examiner

OBESITY ANIMAL MODEL AND METHODS FOR MAKING AND USING THEREOF

This application is the U.S. national phase application of International application number PCT/CN2013/080589, filed on Aug. 1, 2013, which claims the benefit of the filing date of Chinese Patent Application No. 201210280927.6 filed Aug. 8, 2012, the entire disclosure of which is incorporated by reference herein.

TECHNICAL FIELD

The present application relates to biotechnology, particularly relating to methods for making obesity animal models, and the application of such obesity animal models on screening microorganisms, compounds, compositions, drugs, food, formulations or recipes, medicines, nutritional supplements, health care products, or beverages for their role in causing, preventing or treating the obesity.

BACKGROUND

Unless otherwise indicated herein, the materials described in this section are not prior art to the claims in this application and are not admitted to be prior art by inclusion in this section.

A large number of symbiotic microbes live inside the human body, their status and function are equivalent to an important organ acquired after birth, contributing an indispensable role to human health. Within the entire human body, eukaryotic cells accounted for only 10% of the total number of cells; whereas prokaryotic cells accounted for the remaining 90%, thus Nobel laureate Lederberg proposed that the human body is a "super-organism" consisting of both eukaryotic cells and endocommensal symbiotic prokaryotic cells. The endocommensal symbiotic microbes exceed 1000 species, weigh 1-2 kg, and number in the range of 1014, more than 10 times larger than the cell number of the human body, and the number of coding genes is at least 100 times larger than that of human genes.

It is well known that obesity has become an increasingly severe problem of public health in modern society; however, to the present day, the mechanism remains unclear as to how the intestinal flora participate in the onset and development of obesity, insulin resistance and other metabolic diseases. More, it is not clear whether the intestinal flora is the cause or the effect of metabolic diseases; what types of bacteria can lead to the occurrence of metabolic diseases, and what types of bacteria are capable of ameliorating the symptoms of obesity, insulin resistance and other metabolic diseases.

SUMMARY

The following summary is illustrative only and is not intended to be in any way limiting. In addition to the illustrative aspects, embodiments, and features described above, further aspects, embodiments, and features will become apparent by reference to the drawings and the following detailed description.

In one aspect, the present application relates to methods for constructing animal obesity model. In one embodiment, the method includes inoculating animals with an endotoxin (LPS)-producing bacterium under the high-fat diet condition to produce a gnotobiotic animal obesity model. After a microorganism, such as an endotoxin-producing bacterium, or a composition including an endotoxin-producing bacterium, is inoculated into germ-free animals fed with a high-fat diet, the microorganism colonizes within the guts of the germ-free animals. The animals may display obesity, insulin resistance, chronic inflammation, or other symptoms of metabolic disorder, immune system disorder, or other systemic disorders.

In another aspect, the application provides methods for screening microorganism or composition of microorganisms that may cause obesity.

In another aspect, the application provides methods for screening therapeutic targets for treating metabolic disorders such as obesity.

In another aspect, the application provides methods for screening or evaluating microorganisms, food, recipes, formulations, compositions, compounds, drugs, nutritional supplements, healthcare products, beverages, or other items that can be used for preventing or treating metabolic diseases such as obesity.

BRIEF DESCRIPTION OF THE DRAWINGS

The foregoing and other features of this disclosure will become more fully apparent from the following description and appended claims, taken in conjunction with the accompanying drawings. Understanding that these drawings depict only several embodiments arranged in accordance with the disclosure and are, therefore, not to be considered limiting of its scope, the disclosure will be described with additional specificity and detail through use of the accompanying drawings, in which:

FIG. 2A shows the body weight of the *Enterobacter*-associated gnotobiotic model of obesity and the controls; FIG. 2B shows mass of epididymal, mesenteric, subcutaneous inguinal and retroperitoneal fat pad of the *Enterobacter*-associated gnotobiotic model of obesity and the controls; FIG. 2C shows abdominal photographs of the *Enterobacter*-associated gnotobiotic model of obesity and the controls; FIG. 2D shows oral glucose tolerance test (OGTT) and area under the curve (AUC) of the *Enterobacter*-associated gnotobiotic model of obesity mice and the controls; and FIG. 2E shows serum 2 h-post load insulin levels of the *Enterobacter*-associated gnotobiotic model of obesity and the controls; FIG. 3A shows serum LBP levels of the *Enterobacter*-associated gnotobiotic model of obesity and the controls; FIG. 3B shows serum SAA levels of the *Enterobacter*-associated gnotobiotic model of obesity and the controls; FIG. 3C shows serum adiponectin corrected for bodyweight levels of the *Enterobacter*-associated gnotobiotic model of obesity and the controls; FIG. 3D shows reverse transcription (RT)-quantitative PCR analysis of expression of Tnfα, Il1β, Il6, Mcp1, Ikk ε and Tlr4 in the liver of the *Enterobacter*-associated gnotobiotic model of obesity and the controls; FIG. 3E shows reverse transcription (RT)-quantitative PCR analysis of expression of Tnfα, Il1β, Il6, Mcp1, Ikk ε and Tlr4 in the epididymal fat pad of the *Enterobacter*-associated gnotobiotic model of obesity and the controls; and FIG. 3F shows reverse transcription (RT)-quantitative PCR analysis of expression of Tnfα, Il1β, Il6, Mcpl, Ikk ε and Tlr4 in the ileum of the *Enterobacter*-associated gnotobiotic model of obesity and the controls.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The application generally provides, among others, novel methods for constructing animal obesity models, novel methods for screening microorganism or composition of microorganisms that may cause obesity, novel methods for screening therapeutic targets for treating metabolic disorders and novel methods for screening or evaluating microorganisms, compounds, compositions, food, recipes, formulations, drugs, nutritional supplements, healthcare products, beverages, and other items for preventing and treating metabolic diseases.

In one example, the present application provides a method for providing an animal obesity model, in which germ-free animals are inoculated with a microorganism while fed with a high-fat diet. The microorganism may be a single microorganism or a combination of microorganisms. The high fat diet may contain at least 5% fat. The microorganism or the combination may colonize within the guts of the germ-free animals and form the basis of gut microbiota population for the resulting animal models. The animal model may exhibit the symptoms of at least one metabolic or immune system disorders.

The symptoms of metabolic or immune system disorders may be any metabolic syndrome or immune system disorders including, without limitation, obesity, insulin resistance, chronicle inflammation, or non-alcoholic fatty liver disease.

The germ-free animal may be mammals or non-mammals. Example mammals may include a mouse, a rat, a Guinea pig, a pig, a rabbit, or a monkey.

The fat content of the high-fat diet may be at least 5%, at least 10%, at least 15%, at least 20%, or at least 25%.

The microorganism may be a bacterium such as an endotoxin-producing bacterium. The endotoxin-producing bacterium refers to a bacterium capable of producing substance(s) that has endotoxin activity. Example endotoxin-producing bacterium may include, without limitation, B29 strain of *Enterobacter cloacae, Enterobacter cloacae, Enterobacter*, enterobacteriaceae, γ-*Proteobacteria, Proteobacteria*, or Gram-negative bacteria. The microorganism may be in a composition including multiple strains of endotoxin-producing bacteria or including strains of endotoxin-producing and non-endotoxin-producing bacteria. In one example, the microorganism may contain an endotoxin synthesis gene whose sequence is at least 15%, 20%, 30%, 50%, 75% or 95% similar to the B29 strain of *Enterobacter cloacae*.

The animal obesity model provided above may include a gut bacterium having a 16S rRNA gene whose sequence is at least 15%, 20%, 30%, 50%, 75% or 95% similar to SEQ ID NO.1.

The inoculation method as noted above may be any inoculation or administration methods in biological, medicinal, or pharmaceutical fields. Example inoculation methods may include gavage, diets addition, drinking water addition, and smear or topical application of skin or fur. After inoculation, the inoculated microorganisms such as bacteria may colonize in the animal gut, or may be detected in animal feces. In one example, the inoculated bacterial may be continuously detected in the animal feces. The animals may exhibit, among other related metabolic syndromes, weight gain, increased fat, blood lipids, insulin resistance, serum lipopolysaccharide binding protein or leptin resistance, increased serum level of inflammation, or increased inflammatory factor expression levels.

In another aspect, the present application provides methods for screening an obesity-causing microorganism or a combination thereof. In one example, a positive control bacterium that is capable of colonizing the gut of a germ-free animal is inoculated to the animal, which is fed with a high-fat diet. The resulting animal may exhibit at least one type of metabolic or immune system disorders. The said positive control bacterium is compared with a test microorganism or combination thereof. If the test microorganism or a combination thereof exhibits similar effect as the positive control, it is indicative that the test microorganism or combination thereof may cause obesity.

In another aspect, the present application provides methods for screening a microorganism or a combination thereof that has a preventive or therapeutic effect on the symptom of metabolic or immune system disorder. In one example, the method uses an animal model that exhibits at least one symptom of metabolic or immune system disorders. After administering a test microorganism or a combination thereof, if the animal exhibits improvement in at least one symptom of metabolic or immune system disorders, it is indicative that the said microorganism or a combination thereof has a preventive or therapeutic effect on the symptom of metabolic or immune system disorders. In one example, the improvement in at least one symptom of metabolic or immune system disorders may include amelioration of symptom of obesity, insulin resistance, or chronic inflammation. For example, after administering a test microorganism or a combination thereof, if the animal exhibits one or more of weight loss, reduced fat, decreased blood lipids, improved insulin resistance, reduced level of serum lipopolysaccharide binding protein, decreased leptin resistance, decreased serum level of inflammation, or decreased inflammatory factor expression levels, it is indicative that the test microorganism or the combination thereof may have a preventive or therapeutic effect on the symptom of metabolic or immune system disorder.

The test microorganism may be any microorganism. In one example, the test microorganism may include lactic acid bacteria, *Bifidobacteria*, butyrate-producing bacteria, Gram-positive cocci or probiotics.

In another aspect, the present application provides methods for screening a material that may have a preventive or therapeutic effect on the symptom of metabolic or immune system disorders. In one example, the method uses an animal model exhibiting at least one symptom of metabolic or immune system disorders. After administering the material, if the animal exhibits improvement on at least one symptom of metabolic or immune system disorders, it is indicative of that the material may have a preventive or therapeutic effect on the symptom of metabolic or immune system disorders. For example, the improvement may include weight loss, decreased insulin resistance, or reduced chronic inflammation. In one example, after administering the material, if the gnotobiotic animal obesity model exhibits one or more of weight loss, reduced fat, decreased blood lipids, improved insulin resistance, reduced level of serum lipopolysaccharide binding protein, decreased leptin resistance, decreased serum level of inflammation, or decreased inflammatory factor expression levels, it is indicative that the material may have a preventive or therapeutic effect on the symptom of metabolic or immune system disorder.

The above noted material may be edible. For example, the material may include, without limitation, food, recipes, formulations, compounds, compositions, drugs, nutritional supplement, healthcare product, or beverage.

The following examples are for illustration of the execution and property of representative method of the application. These examples are not intended to limit the scope of the application.

Example 1

Materials and Animal Models

Male C57BL/6J mice (germ-free) were used as an example animal. *Enterobacter cloacae* B29 were used as an example inoculation microorganism. The said *Enterobacter cloacae* B29 refers to a superior strain isolated from feces of a morbidly obese patient volunteer. The 16s RNA gene sequence analysis and biochemical assays identified the bacteria as an *Enterobacter cloacae*. 24 healthy male C57BL/6J mice (germ-free) were purchased from Research Diets, Inc. (New Brunswick, N.J.) and fed either on a normal chow diet (NCD, fat content 4.62%, 3.45 kcalories/gram) or high-fat diet (HFD, fat content 34.9%, 5.21 kcalories/gram)

Method on mice: mice were maintained in a 12-hour light cycle (light starting from 6:30 AM) at 22±3° C. Six-ten weeks old sterile mice were randomly distributed into four groups (6 per group), and received the following treatment: (1), NCD+LB group: this group was inoculated by gavage with 0.1 ml sterile LB medium, and fed a NCD; (2) NCD+B29 group: the group was inoculated by gavage with B29 ($10^2$ cells) suspension in 0.1 ml sterile LB medium and fed a NCD; (3) HFD+LB group: this group was inoculated by gavage with 0.1 ml sterile LB medium and fed a HFD; and (4) HFD+B29 group: this group was inoculated by gavage with B29 ($10^2$ cells) suspension in 0.1 ml sterile LB medium and fed a HFD. The experiment lasted 16 weeks. Mice were raised in cages of 3 or 4 in the gnotobiotic isolators, and each mouse's body weight was measured every week. Each group of animals was housed in their own isolators fed with sterile diet and sterile water until euthanasia, and surveillance for bacterial contamination was performed by a periodic bacteriologic examination of the gnotobiotic isolators.

During the experiment, the body weight, fat pad weight, insulin sensitivity and inflammation levels of the mice were monitored.

Example 2

Isolation and Characterization of *Enterobacter cloacae* B29

An analysis of the obese population revealed that a majority of morbidly obese patients suffers from gross imbalance in the gut microbiota. For example, 35% of the total gut bacteria were found to be *Enterobacter* (assayed through 16S rRNA gene library) in a morbidly obese volunteer (26 year old, male, Han ethnicity, body weight 174.9 kg, BMI 58.78 kg/m2). Meanwhile, physical exams showed that the volunteer suffers severe metabolic syndrome. The volunteer underwent 23-weeks of dietary intervention (composition: whole grains, traditional Chinese medicine and prebiotics), when he lost 30.1 kg after 9 weeks, 51.4 kg of 174.8 kg after 23 weeks, and exhibited improvement in all measurement of metabolic syndrome. An analysis of the gut bacteria population revealed that the *Enterobacter* population reduced to 1.8% after 9 weeks on the diet, and became undetectable at the end of the 23-week trialA. *Enterobacter* strains were isolated from the feces of the volunteer via a "sequence-guided-isolation" scheme using LB medium (Luria-Bertani, recipe attached below) at 37° C., obtained the most abundant isolates, and named it B29. Full-length sequencing analysis were performed on 16S rRNA of B29, and it was found that B29 is 99% homologous to *Enterobacter cloacae* (GenBank accession no. AB244457). A biochemical test with VITEK 2 Gram-negative card GN card, bioMerieux, Marcy l'Étoile, France) also indicated that B29 is 98% likely to belong to *Enterobacter cloacae* (Table 1).

Lipopolysaccharide (LPS) were isolated from B29 using a LPS isolation kit from iNtRON Biotechnology Co., Seoul, Korea, and endotoxin activity level was measured using an endotozin activity assay kit LAL (ACC, USA). The result showed that the endotoxin activity of B29 is $4.45 \times 10^6$ EU mg-1 LPS, comparable to *E. coli* strain O55:B5.

In order to perform *Enterobacter cloacae* B29-specific detection, a strain B29 that is resistant to 500 ug/ml Rifampicin was isolated using Rifampicin resistant strains screening method. This strain was inoculated into LB medium and shook for 12 hours under 37° C., and the resulting bacteria culture was used to construct the animal model.

The formula for LB medium (Luria-Bertani) was as follows: tryptone 10 g/L, yeast extract 5 g/L, NaCl 10 g/L, Ph7.4. LB solid medium: 15 grams of agarose were added into 1 L liquid LB medium, heat dissolved, and the medium were poured into plate before cooling.

TABLE 1

Biochemical Characterization of *Enterobacter cloacae* B29 with VITEK 2 ID-GN system

| Well | Abbreviation | Assay | result |
|---|---|---|---|
| 2 | APPA | Ala-Phe-Pro-Arylamidase | − |
| 3 | ADO | Adonitol | + |
| 4 | PyrA | L-Pyrrolydonyl-Arylamidase | − |
| 5 | lARL | L- Arabitol | − |
| 7 | dCEL | D- Cellobiose | + |
| 9 | BGAL | β- d-Galactosidase | + |
| 10 | H2S | H2S production | − |
| 11 | BNAG | β-N-acetyl-glucosaminidase | + |
| 12 | AGLTp | Glutamyl Arylamidase pNA | − |
| 13 | dGLU | D-Glucose | + |
| 14 | GGT | γ- Glutamyltransferase | − |
| 15 | OFF | Glucose fermentation | + |
| 17 | BGLU | β- Glucosidase | (−) |
| 18 | dMAL | D- Maltose | + |
| 19 | dMAN | D- Mannitol | + |
| 20 | dMNE | D- Mannose | + |
| 21 | BXYL | β- Xylosidase | + |
| 22 | BAlap | β- Alanine arylamidase pNA | − |
| 23 | ProA | L- Proline Arylamidase | + |
| 26 | LIP | Lipase | − |
| 27 | PLE | Palatinose | + |
| 29 | TyrA | Tyrosine Arylamidase | + |
| 31 | URE | Urease | − |
| 32 | dSOR | D- Sorbitol | + |

TABLE 1-continued

Biochemical Characterization of *Enterobacter cloacae* B29 with VITEK 2 ID-GN system

| Well | Abbreviation | Assay | result |
|---|---|---|---|
| 33 | SAC | Saccharose/Sucrose | + |
| 34 | dTAG | D- Tagatose | − |
| 35 | dTRE | D- Trehalose | + |
| 36 | CIT | Citric acid salt (sodium) | + |
| 37 | MNT | Malonic acid salts | + |
| 39 | 5KG | 5-Keto-glucoside | − |
| 40 | ILATk | L-Lactate alkalinisation | + |
| 41 | AGLU | α-Glucose | (−) |
| 42 | SUCT | Succinate alkalinisation | + |
| 43 | NAGA | N-Acetyl-β-d-Galactose ammonia-lyase | + |
| 44 | AGAL | α- Galactose glucoside enzyme | + |
| 45 | PHOS | Phosphatase | − |
| 46 | GlyA | Glycine Arylamidase | + |
| 47 | ODC | rnithine decarboxylase | + |
| 48 | LDC | Lysine decarboxylase | − |
| 53 | lHISa | Histidine assimilation | − |
| 56 | CMT | COURMARATE | − |
| 57 | BGUR | β- Glucuronidase | − |
| 58 | O129R | O/129 tolerance | + |
| 59 | GGAA | Glu-Gly-Arg- Arylamidase | − |
| 61 | lMLTa | L- Malate assimilation | − |
| 62 | ELLM | ELLMAN | − |
| 64 | ILATa | L- Lactate assimilation | − |

Example 3

B29 Stable Colonization in the Gut of Germ-Free Mouse

During the experiment, fresh feces samples were collected every two weeks, weighed immediately, and diluted 1:10 in sterile 0.01M PBS. PBS buffer was made according to the following formula: 135 mM NaCl, 2.7 mM KC1, 1.5 mM KH2PO4, and 8 mM K2HPO4, pH 7.2.

Figure 1:
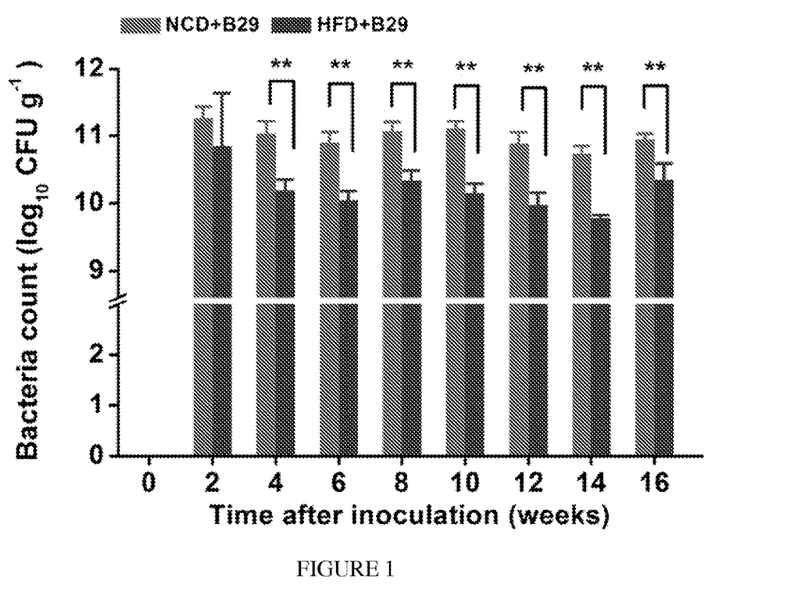
FIG. 1 illustrates the colonization of B29 isolates in gut of germ-free mice fed with a high-fat diet by comparing the population levels of *Enterobacter* sp. B29 in the *Enterobacter*-associated gnotobiotic model of obesity mice with those of the control mice.

Take 100 μl suspension and spread them on LB plates, cultured at 37° C. for 16 hours before counting colonies. The results showed that, during the experiment period (0-16 weeks), the model mice (i.e., HDF+B29) and the NCD+B29 mice all produced feces that contain *Enterobacter cloacae* B29 at the density of $10^{10}$-$10^{12}$ bacteria per gram of wet feces. This result showed that *Enterobacter cloacae* B29 can stably colonize in the gut of germ-free mice after only one inoculation (FIG. 1).

Example 4

B29 Strain Induces Obesity and Insulin Resistance in Mice Fed a High-Fat Diet.

Figure 2:
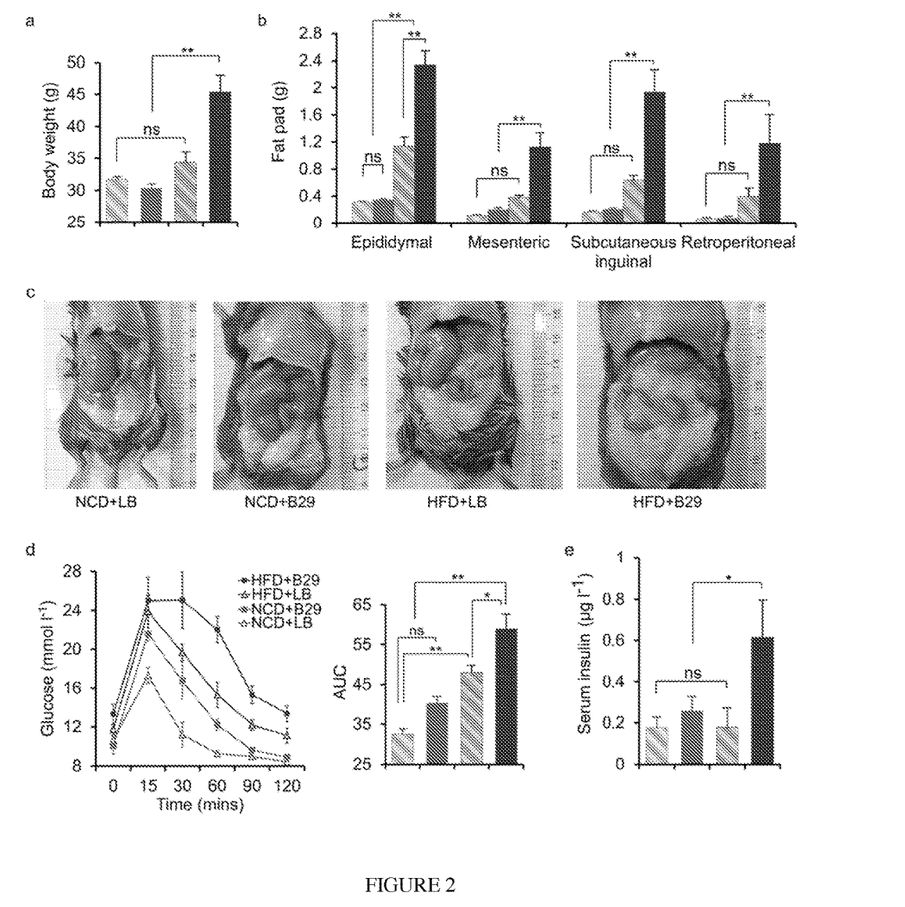
FIG. 2 illustrates B29's effects on obesity and insulin resistance symptoms of germ-free mice fed with a high-fat diet.

During the experiment, the body weight of each mouse was measured accurately with an electronic balance (d=0.01) once a week. On the week 16, mouse was orally administered glucose (2 g/kg body weight) after 5 hours' fasting. Immediately before administering glucose (0 minutes), and 15, 30, 60 and 120 minutes after administering glucose, blood was collected from tail vein, and blood glucose levels were immediately measured by Roche blood glucose meter. These data points were used to calculate the blood glucose tolerance test. 120 minutes after administering glucose, 50 μl blood were collected from retro-orbital vein, left in room temperature for one hour; serum were collected by centrifuge at 3000 rpm for 15 minutes; and blood insulin levels were measured by ELISA (Mercodia, Uppsala, Sweden). This data point represents insulin level two hours after diet. At the end of week 16, mice were dissected under the following procedures. First, open abdomen pictures were taken with rulers as marker on two representative mice from each group; subsequently, epididymal fat pads, mesenteric fat pads, groin subcutaneous fat pads and perirenal fat pads from mice of each group were collected and weighed accurately. Statistical analyses were performed and the results were expressed at average ±S.E.M, using single factor analysis of variance (post Hoc) for statistical significance analysis (Turkey's multiple comparison test, SPSS 17.0). The results are shown in FIG. 2.

The results showed that, the model mice that fed a high-fat diet and received inoculation of *Enterobacter cloacae* B29 exhibited significantly higher body weight than the other three control groups. At the end of 16 weeks, the model mice demonstrated very obvious obesity phenotype. In addition, the results from epididymal fat pads, mesenteric fat pads, groin subcutaneous fat pads and perirenal fat pads demonstrated that the model mice receiving a high-fat diet and inoculation of *Enterobacter cloacae* B29 had very significant weight increases in major fat pads of the mice body. Abdominal dissection pictures demonstrated that the model mice group's body mass and abdominal fat accumulations are obviously larger than those of other groups. Finally, the glucose tolerance of the model group mice is markedly significantly lower than that of other groups, whereas the insulin levels two-hours after diet is significantly higher in the model group compared to other control group.

Example 4

Figure 3:
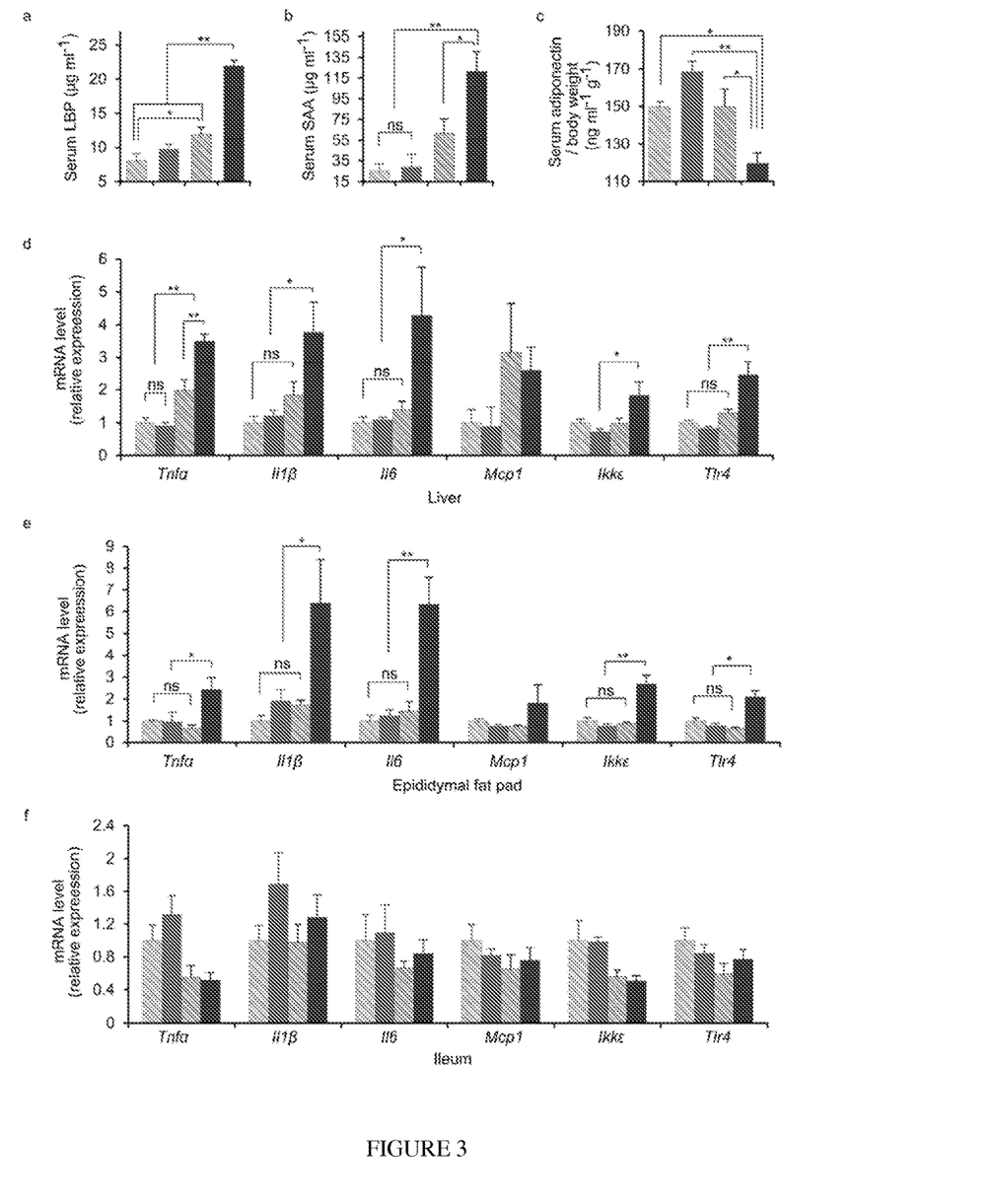
FIG. 3 illustrates B29's effect on level of inflammation of germ-free mice fed with a high-fat diet.

*Enterobacter cloacae* B29's Effects on the Level of Inflammation of Mice Fed a High-Fat Diet In order to demonstrate *Enterobacter cloacae* B29's effects on the level of inflammation in mice fed a high-fat diet, the concentrations of serum lipopolysaccharide binding protein (LBP), serum amyloid A (SAA) protein and adiponectin were measured. The gene expression levels of inflammatory factors in liver, epididymal fat pad, and jejunal tissue were also quantitatively determined. The results are shown in FIG. 3.

The LBP level in obesity model mice (HFD+B29) was significantly higher than that of other groups, despite the numbers of B29 in the gut of mice fed a normal diet far exceeded all other groups. Because B29 was the only LPS-producing bacterium, the significant increase in the endotoxin level in the model mice sera can only derive from B29. The significant increase in the endotoxin level in serum will result in systemic inflammation, which in turn led to insulin resistance and other metabolic disorders symptoms. The obesity model mice showed significant increase in SAA level and significant decrease in adiponectin level, confirming the significant increase in systemic inflammation. The result of gene expression levels of inflammatory factors in liver, epididymal fat pad, and jejunal tissue showed that the obesity model mice had the highest level of expression of TNFα, IL-1β, IL-6, IKK-ε, and TLR4.

Thus, in the obesity model mice that is created based on this application, the serum LBP level and serum SAA level increased significantly compared to the three control groups, adiponectin level decreased significantly compared to the three control groups, and the local tissue expression levels of pro-inflammatory genes increased significantly, compared to the three control groups.

As used in this document, the singular forms "a," "an," and "the" include plural references unless the context clearly dictates otherwise. Unless defined otherwise, all technical and scientific terms used herein have the same meanings as commonly understood by one of ordinary skill in the art.

Nothing in this disclosure is to be construed as an admission that the embodiments described in this disclosure are not entitled to antedate such disclosure by virtue of prior invention. As used in this document, the term "comprising" means "including, but not limited to."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least" and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

DEPOSIT OF BIOLOGICAL MATERIAL

The following biological material has been deposited under the terms of the Budapest Treaty with the China General Microbiological Culture Collection Center, NO. 1 West Beichen Road, Chaoyang District, Beijing 100101, China, and given the following accession number:
Deposit Accession Number Date of Deposit
CGMCC 7.78 2012.11.2

The strain has been deposited under conditions that assure that access to the culture will be available during the pendency of this patent application to one determined by foreign patent laws to be entitled thereto. The deposit represents a substantially pure culture of the deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

What is claimed is:

1. A method for establishing a non-human obesity animal model that develops obesity, the method comprising,
inoculating a non-human germ-free animal with *Enterobacter cloacea* 29, and
feeding the inoculated animal with a diet having at least 34.9% of fat content for a period of time to provide the non-human obesity animal model.

2. The method of claim 1, wherein the non-human obesity animal model manifests a metabolic syndrome comprising at least one of obesity, insulin resistance, or chronic inflammation.

3. The method of claim 1, wherein the non-human obesity animal model is a mouse, a rat, a rabbit, a monkey, a pig, or a Guinean pig.

4. The method of claim 1, wherein the inoculating the non-human germ-free animal comprises inoculating the non-human germ-free animal by at least one of intragastric administration, topical administration, or oral administration.

5. The method of claim 1, wherein the inoculating the non-human germ-free animal comprises inoculating the non-human germ-free animal with at least $10^2$ bacteria cells.

* * * * *

SEQUENCE LISTING

```
<160> NUMBER OF SEQ ID NOS: 1

<210> SEQ ID NO 1
<211> LENGTH: 1464
<212> TYPE: DNA
<213> ORGANISM: Enterobacter
<220> FEATURE:
<223> OTHER INFORMATION:

<400> SEQUENCE: 1 cacccagtc atgaatcaca aagtggtaag cgccctcccg aaggttaagc tacctacttc      60
ttttgcaacc cactcccatg gtgtgacggg cggtgtgtac aaggcccggg aacgtattca     120
ccgtggcatt ctgatccacg attactagcg attccgactt catggagtcg agttgcagac    180
tccaatccgg actacgacgc actttatgag gtccgcttgc tctcgcgagg tcgcttctct    240
ttgtatgcgc cattgtagca cgtgtgtagc cctactcgta agggccatga tgacttgacg    300
tcatccccac cttcctccag tttatcactg gcggtctcct ttgagttccc ggccggaccg    360
ctggcgacaa aggataaggg ttgcgctcgt tgcgggactt aacccaacat ttcacaacac    420
gagctgacga cagccatgca gcacctgtct cagagttccc gaaggcacca aagcatctct    480
gctaagttct ctggatgtca agagtaggta aggttcttcg cgttgcatcg aattaaacca    540
catgctccac cgcttgtgcg ggccccgtc aattcatttg agttttaacc ttgcggccgt     600 actcccagg cggtcgactt aacgcgttag ctccggaagc cacgcctcaa gggcacaacc     660
tccaagtcga catcgtttac ggcgtggact accagggtat ctaatcctgt ttgctcccca    720
cgctttcgca cctgagcgtc agtctttgtc caggggccg ccttcgccac cggtattcct     780
ccagatctct acgcatttca ccgctacacc tggaattcta ccccctcta caagactcta     840 gcctgccagt ttcgaatgca gttcccaggt tgagcccggg gatttcacat ccgacttgac    900
```

-continued

```
agaccgcctg cgtgcgcttt acgcccagta attccgatta acgcttgcac cctccgtatt      960
accgcggctg ctggcacgga gttagccggt gcttcttctg cgggtaacgt caatcgacaa     1020
ggttattaac cttatcgcct tcctccccgc tgaaagtact ttacaacccg aaggccttct     1080
tcatacacgc ggcatggctg catcaggctt gcgcccattg tgcaatattc cccactgctg     1140
cctcccgtag gagtctggac cgtgtctcag ttccagtgtg gctggtcatc ctctcagacc     1200
agctagggat cgtcgcctag gtgagccgtt accccaccta ctagctaatc ccatctgggc     1260
acatccgatg gcaagaggcc cgaaggtccc cctctttggt cttgcgacgt tatgcggtat     1320
tagctaccgt ttccagtagt tatcccctc catcaggcag tttcccagac attactcacc     1380
cgcccgccac tcgtcagcga agcagcaagc tgcttcctgt taccgttcga cttgcatgtg     1440
ttaggcctgc cgccagcgtt caat                                            1464
```